United States Patent [19]
Plant et al.

[11] 4,294,970
[45] Oct. 13, 1981

[54] OXIDATION OF ALPHA-ALKYLATED, BENZYL-SUBSTITUTED 2-THIOPYRIDINE 1-OXIDES

[75] Inventors: Howard L. Plant, Milford; Glenn S. Peterson, Watertown, both of Conn.

[73] Assignee: Uniroyal, Inc., New York, N.Y.

[21] Appl. No.: 118,175

[22] Filed: Feb. 4, 1980

[51] Int. Cl.³ .......................................... C07D 213/62
[52] U.S. Cl. ....................................... 546/294; 71/94
[58] Field of Search ........................................ 546/294

[56] References Cited
U.S. PATENT DOCUMENTS 3,772,307  11/1973  Kaminsky et al. ................. 546/294
4,128,552  12/1978  Wise et al. ......................... 546/294

OTHER PUBLICATIONS

Raphael et al., Advances in Organic Chemistry, vol. 5, Interscience Pub., pp. 2 and 3 (1965).

*Primary Examiner*—Alan L. Rotman
*Attorney, Agent, or Firm*—Anthony Lagani, Jr.; Alfred H. Hemingway

[57] ABSTRACT

A method of oxidizing alpha-alkylated, benzyl-substituted 2-thiopyridine 1-oxides by admixing the compound to be oxidized, a solvent for said compound, acetonitrile, hydrogen peroxide and a base.

10 Claims, No Drawings

OXIDATION OF ALPHA-ALKYLATED, BENZYL-SUBSTITUTED 2-THIOPYRIDINE 1-OXIDES

According to the invention, alpha-alkylated, benzyl-substituted 2-thiopyridine 1-oxides may be oxidized to the respective sulfoxides or sulfones by admixing the compound to be oxidized, a solvent, acetonitrile, hydrogen peroxide and a base.

U.S. Pat. No. 3,960,542, issued June 1, 1976, discloses, inter alia, novel substituted 2-sulfonyl pyridine 1-oxides useful as herbicides. A method of controlling weeds through use of such compounds is disclosed in U.S. Pat. No. 4,019,893, issued Apr. 16, 1977. The disclosures of both of the aforementioned patents are herewith incorporated by reference herein. As taught in both of these patents, the subject compounds may be prepared via formation of intermediate thio compounds, i.e., substituted 2-thiopyridines, and the subsequent oxidation of same to substituted 2-sulfonyl pyridine 1-oxides. Alternatively, the 2-sulfonyl pyridine 1-oxide derivatives may be prepared from known compounds. See, for example, W. Walter et al., Liebig's Ann., 695, 77 (1966); E. Shaw et al., J.A.C.S. 72, 4362 (1050); A. R. Katritsky, J. Chem. Soc., 191 (1957); and U.S. Pat. Nos. 3,107,994 and 3,155,671. Parent 2-thiopyridine 1-oxides may be prepared by (1) the reaction of 2-chloropyridine 1-oxide with the appropriate mercaptan in the presence of an acid acceptor such as an alkaline earth hydroxide; or (2) reaction of the sodium salt of 2-mercaptopyridine 1-oxide with a suitable halide preferentially, but not necessarily, of the benzyl type.

As described in U.S. Pat. No. 3,960,542, one useful synthesis route to the above-described herbicidal compounds involves the oxidation of a 2-thiopyridine prepared by methods described in the literature. The oxidation involves the conversion of both the sulfur and nitrogen to their higher oxidative states in a single preparative step. In this case the products are sulfones as the sequence of oxidation proceeds from sulfide→sulfoxide→sulfone→sulfone N-oxide. The oxidant most generally employed is 30-50% hydrogen peroxide in glacial acetic acid. In excess of three equivalents of peroxide is necessary. Glacial acetic acid and water are noted as being preferred solvents when hydrogen peroxide is used.

In Example 6 of the '542 patent, 2-(1-[2,5-dimethylphenyl]ethyl thio)pyridine 1-oxide is oxidized to the sulfone by admixing the thio compound with chloroform and metachloroperoxybenzoic acid. The metachloroperoxybenzoic acid is, at the present time, too expensive a compound for practical commercial use in oxidizing such thio compounds.

There exist many other known procedures for converting sulfides to sulfoxides and sulfones. These known methods arose primarily to meet specific needs and are tailored to certain structures. The need for tailoring is particularly evident with respect to the compounds herein described. Application of known procedures failed in every instance to give satisfactory yields. Since commercial application of a procedure requires that economic and safety factors be considered, a number of procedures which gave moderate yields, i.e., from about 50 to about 70%, were eliminated as viable routes. A further failing of many of the published methods is that they yield a product comprising an unacceptable, inseparable mixture of sulfoxide and sulfone.

An oxidation reaction for preparing acetamide and oxygen from acetonitrile has been known for some time. Radziszewski, *Ueber die Oxydation mittelst Wasserstoffsuperoxyds*, Berichte, 17, 1289-1290 (1884). More recently, this "Radziszewski Reaction" has been employed in a method for preparing epoxides from olefins. Payne and Williams, *Reactions of Hydrogen Peroxide. VI. Alkaline Epoxidation of Acrylonitrile*, J. Organic Chemistry, 26, 651-659 (1961); *Reactions of Hydrogen Peroxide. VII. Alkali-Catalyzed Epoxidation and Oxidation Using a Nitrile as Co-reactant*, id. at 659-663. However, no evidence of the application of this procedure to sulfur chemistry has been found in the literature.

The invention comprises a process for the oxidation of alphaalkylated, benzyl-substituted 2-thio pyridine 1-oxides having the general formula

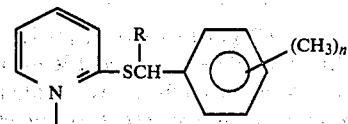

to the corresponding sulfoxides and sulfones, wherein R is alkyl having from 1 to 8 carbon atoms and n is 1 or 2. R is preferably an alkyl group having from 1 to 4 carbon atoms and, in the most preferred application, R is methyl and n is 2. The process comprises admixing the compound to be oxidized, a solvent, acetonitrile, hydrogen peroxide and a base. Preferred solvents include the lower alcohols, such as methanol, propanol and butanol, with the former being most preferred in part because it is relatively easily recovered and recycled. Sufficient base should be admixed to form a mildly alkaline mixture, with a pH of from about 9.0 to about 9.5 being especially preferred.

To allow for the loss of some hydrogen peroxide, somewhat more than the theoretical amount of oxidant must be employed to complete the reaction. In general 2.25 to 2.5 mols of $H_2O_2$ per mol of sulfide to be oxidized to the sulfone is sufficient. Where the sulfoxide rather than the sulfone is desired, using about one-half the amount of solvent, hydrogen peroxide and acetonitrile utilized to obtain the sulfone will result in precipitation of the sulfoxide.

It has been hypothesized that the reaction of mildly alkaline hydrogen peroxide and acetonitrile produces an intermediate percarboximidic acid which then reacts with a substrate, in the instant case a sulfide, to form the sulfoxide and ultimately the sulfone. In the method of this invention, the reaction is necessarily carried out at a somewhat higher pH than is described in the literature, with a resulting secondary reaction involving hydrogen peroxide:

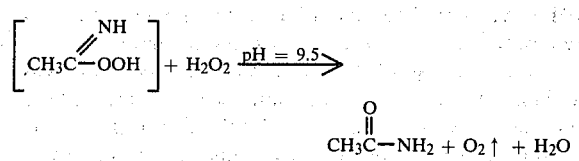

When operating at the preferred pH of about 9.0 to about 9.5, a slow stream of oxygen usually evolves and the rate of oxygen evolution, along with the observed pH, serves as a monitor for preferred operating conditions. The temperature of the reaction may be easily maintained at 30°-40° C. by intermittent application of coolant to a jacket.

The product may be filtered directly from the reaction mixture where it exists as a crystalline slurry. The acetamide impurity is flushed from the cake by water washing and may be recovered from the filtrate for disposal or use. The resulting effluent is ecologically acceptable with a minimum of effort and expense.

The preparation of specific sulfones by methods according to the invention is described in detail in the following examples.

EXAMPLE I

Preparation of 2-[1-(2,5-Dimethylphenyl)ethylsulfonyl] pyridine 1-oxide

A solution of 77.7 gm (0.3 mol) 2-[1-(2,5-dimethylphenyl)ethylthio] pyridine 1-oxide and 30 gm (0.75 mol) acetonitrile in 200 ml of methanol was added to a five necked flask fitted with a stirrer, thermometer, dropping funnel, combination pH electrode and a condenser fitted with a gas bubbler. 50 gm (0.75 mol) of 50% hydrogen peroxide was added gradually with stirring and, as necessary, the admixture was cooled to maintain the temperature at 30° to 35° C.

The system was closed and a 0.5 N solution of sodium hydroxide added with good stirring to obtain the desired pH (approximately 12.5 by meter and 9.0 to 9.5 by paper). A slow gassing at the bubbler of from about 2 to 4 cc per minute served to monitor the pH level in the reactor. As the amount of water in the system increased, the meter readings became truer. Intermittent cooling maintained the temperature at the desired 35°-40° C.

After three hours the level of hydrogen peroxide remaining had become very low and the slurry of sulfone was filtered directly. Washing with five to six fold volumes of water removed the acetamide in the cake and the product air dried to yield 83 gm of product (95% theory).

EXAMPLE II

Preparation of 2-[1-(2,4-Dimethylphenyl)ethyl sulfonyl] pyridine 1-oxide

To a solution of 38.9 gm (0.15 mol) 2-[1-(2,4-dimethylphenyl)ethyl thio]pyridine 1-oxide and 15.6 gm (0.38 mol) acetonitrile in 100 ml of methanol was added sufficient 0.1 N NaOH to obtain the desired pH (approximately 11-12 (meter), 9.0-9.5 (paper)). With good stirring and cooling, as necessary, to maintain a 30°-35° C. reaction temperature, 13 gm (0.19 mol) of 50% hydrogen peroxide was added in increments. The pH dropped and had to be brought back up by the addition of more caustic to maintain the desired pH level. At this pH, oxygen evolved and a bubbler attached to the system served as an indicator of excess alkalinity.

Another 13 gm (0.19 mol) of hydrogen peroxide was added over a period of 15 minutes with cooling and the mixture stirred for an additional hour. Separation of the product started to occur during this period. The reaction mixture was quenched with one liter of cold water, filtered and water-washed to yield a white powder.

Recrystallization from a large volume of ethanol yielded 35 gm pure product having a melting point of 183°-185° C.

EXAMPLE III

Preparation of 2-[1-(2,5-Dimethylphenyl) octyl sulfonyl] pyridine 1-oxide

To a solution of 34.3 gm (0.1 mol) 2-[1-(2,5-dimethylphenyl) octylthio] pyridine 1-oxide and 10.7 gm (0.26 mol) acetonitrile in 400 ml of methanol was added sufficient NaOH solution (6 N to minimize water) to adjust the pH in the operating range of 9.0 to 9.5 (true), approximately 11-12 (meter). 17 gm (0.26 mol) of 50% hydrogen peroxide was added in the same manner as in the preceding example.

The reaction mixture was stirred in excess of 4 hours after peroxide addition. Quenching, filtering and washing yielded 27 gm of product melting at 134-136° C.

We claim:

1. A method of oxidizing alphaalkylated, benzyl-substituted 2-thio pyridine 1-oxides having the general formula

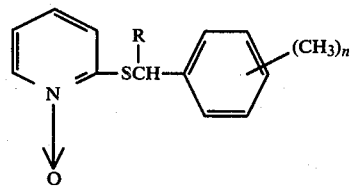

where R is alkyl having from 1 to 8 carbon atoms and n is 1 or 2, said method comprising reacting the compound to be oxidized with acetonitrile and hydrogen peroxide in a solvent for said compound selected from the group consisting of methanol, propanol and butanol, the pH of the reaction mixture being maintained at about 9.0 to about 9.5 with a metal hydroxide.

2. A method according to claim 1, wherein R is alkyl having from 1 to 4 carbon atoms.

3. A method according to claim 2, wherein n is 2.

4. A method according to claim 2, wherein the pH of said admixture is from about 9.0 to about 9.5.

5. A method according to claim 1, wherein R is ethyl and n is 2.

6. A method of making 2-[1-(2,5-dimethylphenyl) ethyl sulfonyl] pyridine 1-oxide, said method comprising the step of admixing 2-[1-(2,5-dimethylphenyl) ethyl thio]pyridine 1-oxide, a solvent for said thio compound, acetonitrile, hydrogen peroxide and a base.

7. A method according to claim 6, wherein the pH of said admixture is from about 9.0 to about 9.5.

8. A method according to claim 7, wherein said solvent is methanol.

9. A method according to claim 7, wherein said base is sodium hydroxide.

10. The method of claim 1 wherein the oxide is 2-(1-(2,5-dimethylphenyl)ethylthio)pyridine 1-oxide thereby producing 2-(1-(2,5-dimethylphenyl)ethyl sulfonyl) pyridine.

* * * * *